(12) United States Patent
Smirnov

(10) Patent No.: US 6,369,399 B1
(45) Date of Patent: Apr. 9, 2002

(54) ELECTROMAGNETIC RADIATION SHIELDING MATERIAL AND DEVICE

(76) Inventor: Igor Smirnov, 3375 Calle Odessa, Carlsbad, CA (US) 92009

( * ) Notice: Subject to any disclaimer, the term of this patent is extended or adjusted under 35 U.S.C. 154(b) by 0 days.

(21) Appl. No.: 09/510,460

(22) Filed: Feb. 22, 2000

(51) Int. Cl.[7] ............................. C23C 28/02; A61N 1/40
(52) U.S. Cl. ................................. 250/515.1; 250/516.1
(58) Field of Search ..................... 250/515.1, 516.1, 250/519.001; 359/885, 886

Primary Examiner—Bruce Anderson
Assistant Examiner—Anthony Quash

(74) Attorney, Agent, or Firm—Brown Martin Haller & McClain

(57) ABSTRACT

A material and devices made therefrom are described when placed in proximity to persons, animals and plants serve to lessen adverse health effects caused by electromagnetic radiation (EMR) exposure. The material has a polymeric matrix and inorganic and organic components which are responsive to an magnetic field and emitting natural electromagnetic oscillations which are beneficial to humans, animals and plants, and offset harmful aspects of the EMR. The polymer is polar and has high relative permitivity. The components are an oxydated hydrocarbon emulsifier; a galvanic salt; an alkaloid; a dye or stain; and a polysaccharide. The devices may be solid, fibrous, powdered or woven fabrics.

18 Claims, 1 Drawing Sheet

ELECTROMAGNETIC RADIATION SHIELDING MATERIAL AND DEVICE

BACKGROUND OF THE INVENTION

1. Field of the Invention

The invention herein relates to exposure of living organisms to electromagnetic radiation (EMR). More particularly it relates to materials to reduce the harmful physiological effects that extended exposure to EMR may pose to the humans, animals and plants and devices made therefrom.

2. Description of the Prior Art

EMR is emitted by every operating electrical and electronic device. The power of EMR emission varies depending on the size and electrical strength of the device and the electrical current it carries or employs. High voltage power lines are significant emitters of EMR, and field strengths sufficiently high to have the potential for causing adverse EMR effects in humans, animals and plants can be detected hundreds of feet away. Smaller devices such as computers, television sets, microwave ovens and the like emit lesser quantities of EMR, but the effect on humans can still be significant because people are in much closer proximity to such devices.

While there has been controversy over whether significant health effects in humans has been proven or disproved by various studies, there is no doubt that EMR fields do surround power lines and common electrical and electronic devices. It is therefore the desire of many prudent people to protect themselves, their animals and plants against whatever health risks might be involved by their exposure to EMR over extended periods of time. Unfortunately, effective and convenient devices for shielding against EMR have not been generally available. Essentially the only defense against EMR has been removal of persons, animals and plants from proximity to the EMR-emitting devices. For major emitters such as power lines or electrical substations, this has usually meant that one has had to move to a different house or to a different job location away from the power line or substation, which commonly means substantial expense and inconvenience. The adverse costs and inconveniences are similar to farmers and ranchers who must move animals and crops to locations remote from the power lines or stations. For devices such as microwave ovens or computers, it has meant that a person must sit or stand at an awkward distance from the device, which can impair the person's ability to use the device in an optimum manner.

Because there is a magnetic field component to EMR, conventional shielding which might provide protection against electrical shock is not effective to shield against the effects of the generated magnetism on a human, animal and plant bodies and health.

Adverse human health effects which have been reported as attributable to long-term EMR exposure include occurrence of certain cancers, multiple sclerosis and autism. Reported adverse effects on animals have included stillbirths of young and reduction of milk production in cattle.

It would therefore be advantageous if there were a device available which could effectively shield people, animals and plants against harmful, adverse health consequences which may be inherent in prolonged or extended exposure to EMR.

SUMMARY OF THE INVENTION

I have now invented a material which may be fabricated in numerous embodiments and which when worn, carried or otherwise kept in proximity to persons, animals and even plants, serves to lessen adverse health effects caused by EMR from power lines, computers, mobile telephones, microwave ovens, televisions and numerous other electrical and electronic devices. These EMR shielding materials and devices can be fabricated and used in many different embodiments. This enables the invention to be used effectively in many locations and under many circumstances where prior art devices were simply unavailable or ineffective.

Key to the present invention is a polymeric body into which are incorporated small quantities of inorganic and organic materials, those materials when placed in an EMR magnetic field, respond to that EMR by emitting natural electromagnetic oscillations which are beneficial to humans, animals and plants, and which at least in part counteract the harmful aspects of the EMR on the human, animal or plant. The polymeric material may be formed into devices of a wide variety of embodiments, including block solids, fibers, fabrics, particulate, and so forth.

Specifically, the invention herein comprises a material to reduce adverse effects of electromagnetic radiation exposure of a human, animal or plant body, comprising a polymeric matrix having high relative permitivity and having incorporated therein a) an oxydated hydrocarbon emulsifier; b) a galvanic salt; c) an alkaloid; d) a dye or stain; and e) a polysaccharide; the material upon exposure to incident electromagnetic radiation responding thereto by emission of electromagnetic oscillations at frequencies which counter the adverse effects of the incident electromagnetic radiation on the body. In a preferred embodiment the polymer is an epoxy polymer.

In preferred embodiments the material's composition comprises, in parts per 1000 parts by weight of the polymer:

| | |
|---|---|
| the oxydated hydrocarbon emulsifier | 10 mL |
| the galvanic salt | 1.3 parts by weight |
| the alkaloid | 2.6 parts by weight |
| the dye or stain | 2.3 parts by weight |
| the polysaccharide | 1.2 parts by weight. |

The material may be disposed in a variety of different forms, but the common ones will be as unitary solid objects, often as small disks, or as fibers from which fabrics or garments may be woven.

Other aspects and embodiments of the present invention will be evident from the disclosure below.

DETAILED DESCRIPTION AND PREFERRED EMBODIMENTS

Figure 1:
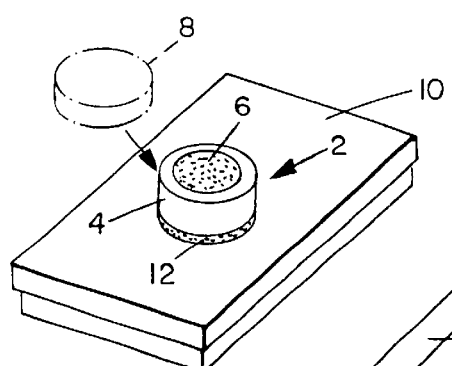
FIG. 1 is a perspective view of one embodiment of a device formed of the polymeric body of the present invention, and attached for convenience to a common object.

In its most basic form, the invention here is a polymeric material in which the polymeric matrix contains small concentrations of several different types of components—an oxydated hydrocarbon emulsifier, a galvanic salt, an alkaloid, a dye or stain, and a polysaccharide. Collectively these components and the polymer form a unique composition which has the unusual ability, when activated by exposure to EMR, to generate its own electromagnetic oscillations at frequencies which resonate with cellular structures and effectively counteract the harmful aspects of the EMR. Thus when a person, animal or plant is exposed to EMR, having a device made of the present material on one's person or in close proximity will reduce the harmful effects which one may suffer from prolonged exposure to the EMR. As an example presented below shows, substantial reductions in the adverse effects on human blood by EMR exposure can be obtained by having a device made of the present material present in proximity to the exposed blood.

The polymer which forms the matrix of the present can be any polar thermosetting or thermoplastic polymer which has a high value of relative permitivity (dielectric constant). Numerous polar polymers are described in the literature; of particular preference in the present compositions are the epoxy polymers. As the matrix, the polymer will form the bulk of the present materials. The concentrations of the components discussed below are stated with respect to 1000 mg of the polymer.

A first component of the material is an emulsifier having solvent properties, which facilitates the incorporation of the components into the polymeric matrix. Numerous suitable emulsifiers are disclosed in the literature. Preferred in these compositions are glycol ethers or salts thereof. A particularly useful emulsifier is ethylene glycol monobutyl ether or its acetate salt (both available commercially under the respective trade names "Butyl Cellusolve" and "Butyl Cellusolve Acetate"). The emulsifier will be present in a concentration of 1–25 milliliters, preferably about 10 mL.

A second component is a galvanic salt which imparts galvanic properties to the composition. Numerous inorganic (and some organic) salts may be used, including the alkali metal and alkaline earth metal salts. The more reactive salts such as the sodium salts are preferred. The anions of the salts may be galvanically active ions such as the various forms of phosphates. Particularly preferred is dibasic sodium phosphate. The galvanic salt will be present in a concentration of 0.1–3.0 mg., preferably about 1.3 mg.

The third component will be an alkaloid which has parasympatholytic properties, and thus counteracts stimulation of the parasympathetic nervous system. Preferred alkaloids are atropine and its derivatives. Particularly preferred is tropine ($C_8H_{15}NO$) which is obtained by hydrolysis of atropine. The alkaloid will be present as 1.0–5.0 mg, preferably about 2.5–2.7 mg.

The fourth component will be a dye or stain, preferably fluorescein or a derivative thereof. Particularly preferred is rose bengal ($C_{20}H_2O_5I_4Cl_4Na_2$), also known as 4,5,6,7-tetrachloro-2,4',5'7'-tetraiodofluorescein (sodium salt) and as "Acid Red 94". The dye or stain will be present as 0.5–3.0 mg, preferably about 2.0–2.5 mg.

Finally, the basic compositions herein will also contain a polysaccharide, preferably a phycocolloid. Particularly preferred are the phycocolloids derived from algae, such as seaweed. Preferred is agar (also known as agar-agar), which is a phycocolloid derived from the red algae such as Gelidium or Gracilaria and is a polysaccharide mixture of agarose and agaropectin. The polysaccharide will be present as 0.1–3.0 mg, preferably 1.0–1.5 mg.

The polymeric materials of this invention are easily manipulated and can be formed into a wide variety of shapes and have a variety of different sizes. Two types of embodiments have been found particularly useful; see FIGS. 1–3. The first is to have the material formed as a unitary small device, such as a disk 2. In the embodiment shown in FIG. 1, the disk is formed as a hollow cylinder about 1" (2.5 cm) in diameter and ½' (1.2 cm) high with a wall 4 which forms a container into which the material 6 is placed. The material 6 being in a liquid form before the polymerization can be placed into the hollow interior where it hardens because of the polymerization reaction, or it can be in granular or powdered form and be packed into the interior. A cover 8 (shown in phantom) may be placed onto the disk 2 after placement of the polymeric material 6 if desired, but the cover is not required. The disk 2 may conveniently be mounted on a common object that a person would carry on his or her person or in a purse, such as a box 10 (perhaps a compact, keycase or the like), by use of a layer of adhesive 12. Larger or small versions of the disk may also be used.

Figure 2:
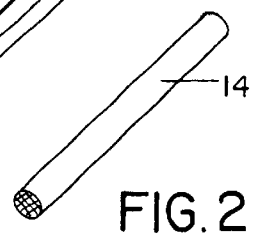
FIG. 2 is an oblique view of a polymeric material of the present invention in the form of a fiber.
Figure 3:
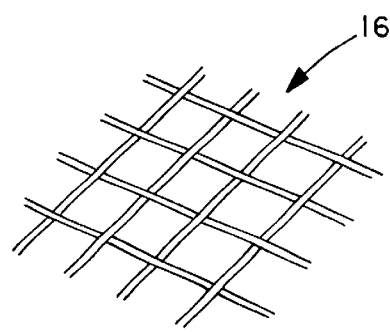
FIG. 3 is a schematic, oblique enlarged view of a portion of a woven fabric containing fibers of FIG. 2.

In the alternative embodiment shown in FIGS. 2 and 3, the polymeric material is formed (such as by extrusion) into a fibrous form 14 from which it can be woven into a fabric 16. The individual fibers in the fabric 16 may all be made of the polymeric composition, but more preferably fibers of the polymeric composition will be distributed among a larger number of fibers of conventional fabric materials such as cotton or wool. Since the compositions of this invention are effective in relatively small quantities, as evident from the description of the disk 2 above, it will be understood that the fabric can be made into a garment to be worn, in which the garment is largely composed of the conventional fibers in the fabric, and that fibers of the present polymeric composition are a minor part of the actual garment.

While the mechanism of operation of the present materials and devices made therefrom is not known exactly, it is believed that the following may be applicable (but is not to be construed as limiting of the invention). The polar nature of the polymer allows both bonding and non-bonding electrons in the molecular structure of the polymer to be readily displaced by exposure to an external electromagnetic field. Thus the external electromagnetic field of the EMR creates in the molecular structure of the polymeric composition the excitation of electromagnetic forces which in turn amplifies the corona discharge effect of the polymer and assortment components. The result of this amplification is an emission of subtle electromagnetic oscillations originated by the polymer itself. It is these subtle electromagnetic oscillations which are beneficial to the adjacent human, animal or plant bodies and which serve to counteract or compensate for the negative effects on the various bodies. The recent discoveries in biophysics proved that certain subtle low frequencies can resonate with cellular structures and improve cellular function and metabolism. The different combinations of the inorganic and organic components incorporated into the polymeric matrix cause variations in the frequencies of the electromagnetic oscillations of the polymer, and thus produce varying effects in the different human, animal and plant organisms.

The beneficial effects of this material on humans exposed to EMR is illustrated by the following example. Blood samples were taken from twenty-two adult subjects. Each sample was divided into three parts. The first part was used as a control and was not exposed to EMR. The two remaining parts were exposed to the VLF (very low frequency) EMR emitted by an operating 14" computer monitor screen for one hour, positioned at a person's normal viewing distance of the screen. One of the two remaining parts was exposed to that VLF EMR without any shielding being present. The other part was exposed to that VLF EMR while a sample of the present material in the form of a solid body was positioned proximate to and directly below the screen. The specific composition used comprised an epoxy polymer with the following components (usually reported as mg per 1000 mg of the epoxy polymer): ethylene glycol monobutyl ether ("Butyl Cellusolve": 10 mL), sodium phosphate (1.3 mg), tropine (2.6 mg), rose bengal (2.3 mg) and agar (1.2 mg). After separation all three groups of sample parts were subjected to standard blood testing. The test and their results (N=22) are reported in the Table below. The tests, as abbreviated in the Table, were as follows:

TABLE

Blood Test Results

| Test | Control | Radiated Shielded | % Dif. | Radiated; Unshielded | % Dif. |
|---|---|---|---|---|---|
| WBC | 6.6 K/µL | 6.7 K/µL | +1.5 | 6.6 K/µL | 0 |
| LYM | 36.0% | 44.3% | +23 | 49.4% | +37 |
| MID | 18.0% | 23.7% | +31 | 24.2% | +34 |
| GRAN | 46.0% | 32.0% | −30 | 26.4% | −43 |
| RBC | 4.50 M/µL | 6.34 M/µL | +41 | 4.83 M/µL | +7 |
| HGB | 13.8 g/dL | 14.6 g/dL | +6 | 14.9 g/dL | +8 |
| HCT | 28.7% | 43.7% | +52 | 44.5% | +55 |
| MCV | 92 fL | 92 fL | 0 | 92 fL | 0 |
| MCH | 30.7 pg | 30.7 pg | 0 | 30.8 pg | +0.3 |
| MCHC | 32.1 g/dL | 33.5 g/dL | +4 | 33.5 g/dL | +4 |
| RDW | 14.2% | 14.4% | +1 | 14.4% | +1 |
| PLT | 208 K/µL | 193 K/µL | −7 | 197 K/µL | −5 |

Figure 5:
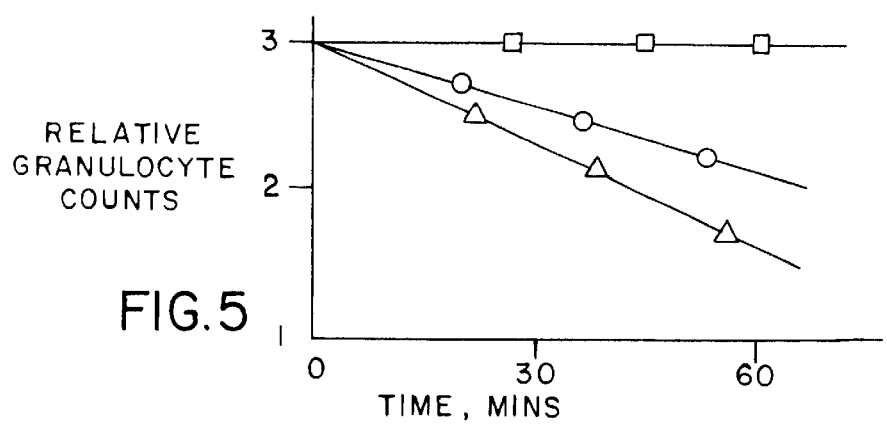
FIGS. 5 and 6 illustrate graphically the positive results obtained in blood tests involving use of the material of this invention to reduce the harmful effects of EMR exposure to human subjects.
Figure 6:
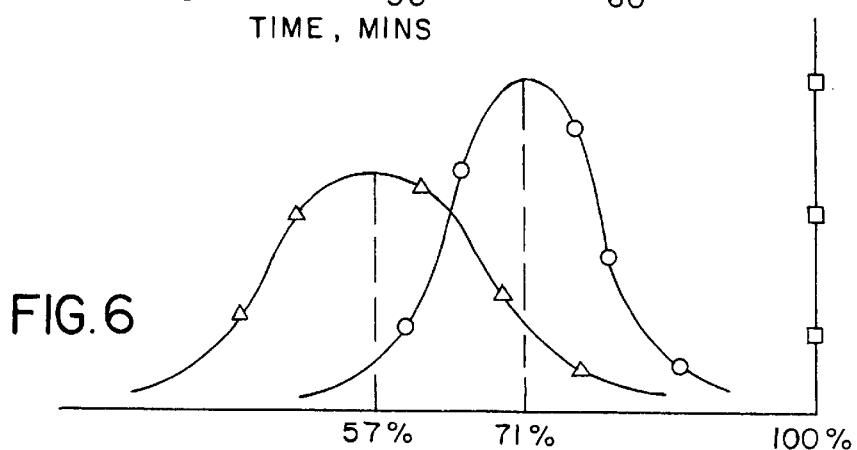

WBC White blood cell count
LYM Lymphocyte count within WBC
MID "Minimum inhibitory dilution," an aspect of the Schlichter Test, and a measure of the presence of less frequently occurring and rare cells correlating to monocytes, eosinophils, basophils, blasts and other precursor white cells.
GRAN Granulated cell count within WBC, corresponding to the granuloctytes, i.e., basophils, eosinophils and neutrophils.
RBC Red blood cell count
HGB Hemoglobin content
HCT Hematocrit
MCV Mean corpuscular volume
MCH Mean corpuscular hemoglobin
MCHC Mean corpuscular hemoglobin concentration
RDW Red cell distribution width
PLT Platelet content The striking result which is evident from the above data, and which is reflected graphically in FIGS. 5 and 6, is the significant reduction in the decline of granulocyte content of the blood which was irradiated but shielded by the presence of the material of this invention. FIG. 5 illustrates the decline in granulocyte count in blood samples exposed to EMR for one hour without (—△—) and with (—○—) shielding by the material of this invention, as compared to the granulocyte content of the non-exposed control samples (—□—). FIG. 6 reflects the same data and illustrates the spread of the decline of the individual samples. As compared to the control the shielded group had one-third less decline in granulocyte content from the EMR exposure than did the non-shield group. Since granulocytes are a critical component of blood, and play one of the most important roles in the immune systems of the body. it is evident that the presence of the material of this invention protected the blood samples from significant amounts of harmful effects (i.e., content decline of granulocytes) resulting from the EMR exposure. The special point of interest is the significant increase of the red blood cells (RBC) in the shielded group. These cells play the major role in the process of oxygenation of the body. This result shows that the installation of the shielding device can positively affect the process of cellular oxygenation and as a result improve metabolism.

The increase of lymphocytes above normal level can also contribute to some negative effects such as leukemia, lymphomas, skin rash, etc. As compared to the control group the shielded group has about 40% less increase in lymphocytes content than the non-shielded group.

Figure 4:
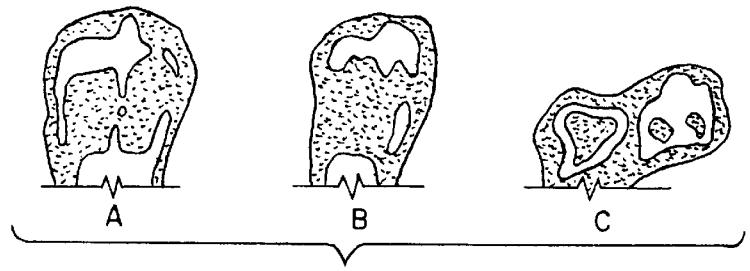
FIG. 4 illustrates pictorially the effects on plant leaves of use of the present material to reduce the harmful effects of EMR exposure of the plant.

Another example of the effectiveness of the present compositions is illustrated in FIG. 4. The three views in this Figure are drawings of photographs of the leaves of a plant made by high-voltage photography. High-voltage photography is a process which allows the corona discharge effect of a body to be detected and captured for visual observation. The first view A is of the coronal discharge of a typical leaf of the plant before exposure to the VLF EMR from the computer monitor mentioned above. The solid image of the leaf indicates that all of the cells of the leaf are alive and functioning. In view B a leaf was exposed to the EMR for 30 minutes but in the presence of a shielding device of the present invention. The detect coronal discharge shows that about 80% of the cells have survived. In contrast, in view C, which shows a leaf exposed for the same 30 minutes but without the presence of the shielding device, in which only 40% of the cells have survived.

It will be evident that there are numerous embodiments of the present invention which are not expressly described above, but which are clearly within the scope and spirit of the invention. The above description is therefore to be considered exemplary only, and the actual scope of the invention is to be defined solely by the appended claims.

I claim:

1. A material to reduce adverse effects of electromagnetic radiation exposure of a human, animal or plant body, comprising a polar polymeric matrix having high relative permitivity and having incorporated therein:

a. an oxydated hydrocarbon emulsifier;

b. a galvanic salt;

c. an alkaloid;

d. a dye or stain; and e. a polysaccharide;

said material upon exposure to incident electromagnetic radiation responding thereto by emission of electromagnetic oscillations at frequencies which counter said adverse effects of said incident electromagnetic radiation on said body.

2. A material as in claim 1 wherein said polymeric matrix comprises an epoxy polymer.

3. A material as in claim 1 wherein said emulsifier comprises a glycol ether or salt thereof.

4. A material as in claim 1 wherein said polysaccharide comprises a phycocolloid.

5. A material as in claim 1 wherein said galvanic salt comprises an inorganic salt.

6. A material as in claim 4 wherein said inorganic salt comprises an inorganic phosphate.

7. A material as in claim 1 wherein said alkaloid comprises a parasympatholytic agent.

8. A material as in claim 7 wherein said parasympatholytic agent comprises an atropine derivative.

9. A material as in claim 1 wherein said dye or stain comprises fluorescein or a derivative thereof.

10. A material as in claim 9 wherein said dye or stain comprises a polyhalogen-substituted fluorescein.

11. A material as in claim 1 comprising, in parts per 1000 parts by weight of said polymer:

| | |
|---|---|
| said oxydated hydrocarbon emulsifier | 1–25 mL |
| said galvanic salt | 0.1–3.0 parts by weight |
| said alkaloid | 1.0–5.0 parts by weight |
| said dye or stain | 0.5–5.0 parts by weight |
| said polysaccharide | 0.1–3.0 parts by weight. |

12. A material as in claim 11 comprising, in parts per 1000 parts by weight of said polymer:

| | |
|---|---|
| said oxydated hydrocarbon emulsifier | 10 mL |
| said galvanic salt | 1.3 parts by weight |
| said alkaloid | 2.6 parts by weight |
| said dye or stain | 2.3 parts by weight |
| said polysaccharide | 1.2 parts by weight. |

13. A material as in claim 12 wherein said polymer comprises an epoxy polymer and further comprising, in parts per 1000 parts by weight of said epoxy polymer:

| | |
|---|---|
| ethylene glycol monobutyl ether | 10 mL |
| sodium phosphate | 1.3 parts by weight |
| tropine | 2.6 parts by weight |
| rose bengal | 2.3 parts by weight |
| agar-agar | 1.2 parts by weight. |

14. A material as in claim 1 formed as a unitary solid body.

15. A material as in claim 14 formed as a plurality of said solid bodies in the form of individual granules, said granules being disposed adjacent to each other as a constrained mass of form defined by a constraining container.

16. A material as in claim 1 formed as a fiber.

17. A material as in claim 16 comprising a woven fabric comprising a plurality of said fibers.

18. A material as in claim 17 comprising a woven fabric comprising a plurality of said fibers and fibers from at least a second type of fiber.

* * * * *